United States Patent [19]
Beckman et al.

[11] Patent Number: 5,177,993
[45] Date of Patent: Jan. 12, 1993

[54] AIR-IN-LINE SENSOR

[75] Inventors: Kenneth A. Beckman; James E. Dikeman; Simon E. Finburgh, all of San Diego, Calif.

[73] Assignee: IVAC Corporation, San Diego, Calif.

[21] Appl. No.: 733,310

[22] Filed: Jul. 22, 1991

[51] Int. Cl.$^5$ .................... G01N 29/02; G01N 33/49
[52] U.S. Cl. ................... 73/19.03; 73/19.1; 128/DIG. 13
[58] Field of Search ............ 73/19.03, 19.1, 600, 73/632; 128/DIG. 13

[56] References Cited

U.S. PATENT DOCUMENTS

| | | | |
|---|---|---|---|
| 3,921,622 | 11/1975 | Cole | 128/660.01 |
| 3,985,133 | 10/1976 | Jenkins et al. | 128/DIG. 12 |
| 4,068,521 | 1/1978 | Cosentino et al. | 73/19.03 |
| 4,112,773 | 9/1978 | Abts | 73/19.1 X |
| 4,114,144 | 9/1978 | Hyman | 340/632 |
| 4,418,565 | 12/1983 | St. John | 73/19.03 |
| 4,504,263 | 3/1985 | Steuer et al. | 128/DIG. 13 |
| 4,551,134 | 11/1985 | Slavik et al. | 128/DIG. 13 |
| 4,559,454 | 12/1985 | Kramer | 250/577 |
| 4,607,520 | 8/1986 | Dam | 73/19.1 X |
| 4,722,224 | 2/1988 | Scheller et al. | 73/600 X |
| 4,881,413 | 11/1989 | Georgi et al. | 73/861.12 |
| 5,003,516 | 3/1991 | Sato et al. | 367/150 |
| 5,123,275 | 6/1992 | Daoud et al. | 73/19.03 |

FOREIGN PATENT DOCUMENTS 2240342 3/1974 Fed. Rep. of Germany ..... 73/19.03

*Primary Examiner*—Hezron E. Williams
*Assistant Examiner*—Joseph W. Roskos
*Attorney, Agent, or Firm*—Fulwider, Patton Lee & Utecht

[57] ABSTRACT

An air-in-line sensor is provided comprising an adapter for insertion in the fluid line and a sensor housing. The adapter is semi-compliant and includes convex-shaped acoustic coupling surfaces for engaging the straight and rigid transducer sensing walls of the housing. The convex surfaces of the adapter have a larger diameter than the distance between the housing sensing walls and an interference fit results. Due to this interference fit, the shape of the coupling surfaces, the varying thicknesses of the adapter walls and the difference in compliance of the materials of the adapter and the housing, a more uniform contact pressure profile is provided. The upper part of each sensing channel wall in the housing includes a ledge which wipes contaminants from the coupling surfaces of the adapter as it is inserted into the sensor channel of the housing. The inner passage of the adapter in the sensing section is tapered and this shape resists bubbles which may otherwise tend to adhere to the interior surface of the adapter and be detected by the transducers.

19 Claims, 3 Drawing Sheets

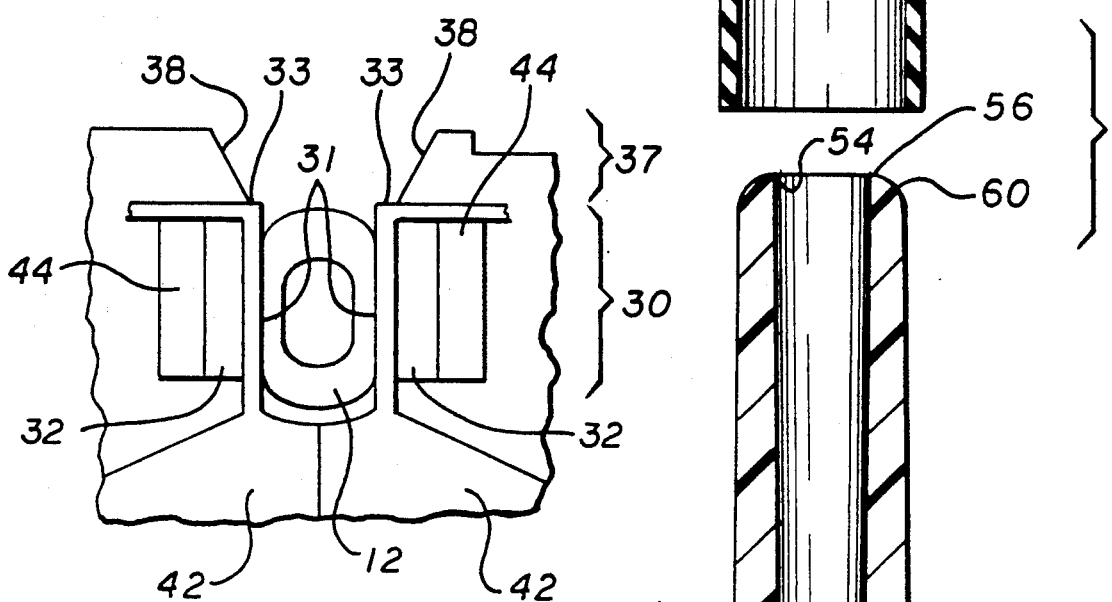
FIG. 3
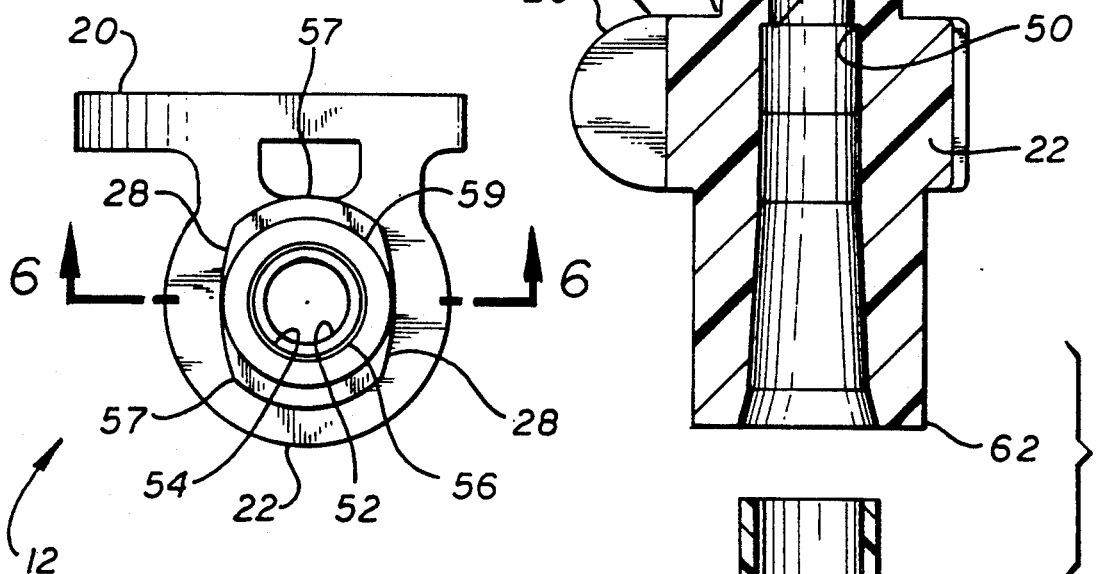
FIG. 5
FIG. 6

AIR-IN-LINE SENSOR

BACKGROUND

The invention is related generally to sensors and more particularly to fluid line sensors for monitoring the existence and contents of a fluid line.

Air-in-line sensing systems typically include a pair of transducers positioned opposite each other, between which is disposed a fluid line to be sensed. One of the sensors is used to transmit ultra-sonic acoustic energy and the other is used to receive the energy. The fluid line interacts with that transmitted acoustic energy and that interaction is detected by the reveiver transducer. The output of the receiver transducer can be processed to determine certain properties of the fluid in the sensed fluid line.

Such a sensor system has had an application in the medical field. Because an air bubble of sufficient size has the potential to cause death in a patient if infused, air-in-line sensor systems are routinely used to sense for the existence of air in intravenous infusion lines. The acoustic impedance of intravenous infusion solutions is readily discernable from the acoustic impedance of air. Air positioned between the transducers increases the impedance between those transducers and results in a reduction in the output of the receiver transducer. Upon detecting an air bubble of a particular size, an alarm is provided and the infusion pump operation is stopped.

One requirement of acoustic air-in-line sensor systems is that firm and as uniform as possible tubing-to-transducer contact be made so that only air bubbles residing inside the fluid line are detected. If poor contact exists, air may reside between the outside surface of the tubing and a transducer. The sensor will be unable to determine if this air is inside the tubing or outside. Air outside the tubing but in the sensing path will result in a decrease in the signal-to-noise ratio of the sensor system or worse, an air-in-line alarm. Because of this undesirable consequence, great effort has been applied to developing the geometries of transducer-to-tubing interfaces to obtain firm and uniform contact. In cases where the tubing is over-compressed in the sensor, it has been noticed that the contact pressure between the tubing and the transducer diminishes in some areas and may even cease to exist thereby allowing air between the exterior of the tubing and the sensor.

Some prior sensing systems comprise a channel into which the fluid line is pressed and comprise transducers located on opposite sides of the channel which face each other. In these systems, the same type of fluid line operated on by the associated controller or pumping mechanism is sensed by this air-in-line sensor system.

In the case where the controller or pump comprises a peristaltic mechanism, the fluid line is formed of a compliant material so that the peristaltic pumping mechanism can occlude the tubing along a pumping zone. Silicone or PVC tubing is typically used. If no strain relief is included between the pumping mechanism and the following air-in-line sensor, the mechanical action of the closer peristaltic fingers may cause a change in the dimensions of the tubing sensed by the air-in-line sensor and the performance of the air-in-line sensor may degrade. Such a result can occur where the air-in-line sensor is located so close to the last fingers of the pump that the fingers pull the tubing into a deformed shape during occlusion and this shape change extends into the air-in-line sensor segment of the tubing. Additionally, typical fluid tubing subjected to heat and the continuous contact pressure in an air-in-line sensor loses its resiliency and the contact pressure between it and the air-in-line sensor may diminish thereby degrading the performance of the sensor. Tubing manufacturing tolerances which vary significantly also pose difficulty in the design of the air-in-line sensor.

Another problem affecting prior air-in-line sensor systems is the presence of contamination adhering to the segment of tubing being sensed. Infusion fluids or other fluids or particulate matter reaching the outside of the fluid line either through handling of the fluid line or through leaking fluid couplings located above the sensed segment can affect the transmission of the acoustic energy between the transducers and may decrease the accuracy of air-in-line detection. It would be desirable to provide a sensing system which is resistant to external fluid line contamination.

A further problem affecting some air-in-line sensing systems is the interference with the sensing process caused by nuisance air bubbles which either become transfixed on the interior tubing wall at a position between the transducers, or move between different positions inside the tubing in the path of the sensing energy of the transducers. In many cases, an original transfixed air bubble alone is not large enough to cause an air-in-line alarm if detected but these bubbles tend to grow in size and after reaching a certain size, can significantly interfere with the sensor. Air bubbles which oscillate between positions in the sensing segment can also grow and their presence can lower the effectivity of the sensor.

It has been found that silicone tubing, which is commonly used as the pumping segment of the fluid line with peristaltic pumps, is permeable enough to allow air bubbles to enter the tubing which has an inside surface promoting attachment of the air bubbles to that surface. It has also been noted that such air bubbles tend to cling to the inside surface of PVC tubing as well. In the case where the fluid line is oriented vertically and low pump rates are used, such bubbles may move from a point upstream in the fluid line to a point downstream in the fluid line and then float back upstream again. It would be desirable to provide an air-in-line sensor system which resists the formation of nuisance bubbles.

Hence, those concerned with air-in-line sensor systems have recognized that it would be of value to provide a system which is not susceptible to degradation due to its placement next to the pumping mechanism. It would also be of value to provide a system which is not sensitive to tubing tolerance variations and which does not experience reduced performance when subjected to heat and continued contact pressure. It would also be of value to provide a system which resists the formation of transfixed or oscillatory air bubbles between the transducers. The present invention fulfills these needs.

SUMMARY OF THE INVENTION

In accordance with the invention, an air-in-line sensor is provided which comprises a fluid line adapter for inclusion in the fluid line and comprises a sensor housing having a sensing channel for receiving the adapter. The sensor housing includes transducers located opposite each other across the sensing channel for sensing the existence of the adapter and for sensing properties of the fluid in the adapter. The adapter and housing have shapes selected so that the adapter will firmly fit into the sensing channel with a predetermined orientation and will develop a more uniform pressure profile between the adapter and the sensing channel to which the transducers are acoustically coupled.

The adapter includes outwardly-facing acoustic coupling surfaces located diametrically opposite each other. The walls of the sensor housing are flat and parallel in one embodiment and are separated from each other by a distance which is less than the diameter of the acoustic coupling surfaces of the adapter, thus resulting in an interference fit. In one embodiment, the adapter is formed of a semi-compliant material and the walls of the sensing channel are formed of a rigid material. Due to the adapter's shape and size and semi-compliant material composition, it is reshaped when inserted into the sensing channel of the sensor housing to result in a more uniform pressure profile between the acoustic coupling surfaces of the adapter and the sensing channel walls.

The adapter is generally circular in cross section except for the coupling segment which contains the acoustic coupling surfaces. The acoustic coupling surfaces are convex in shape and the adapter walls on which the coupling surfaces are formed are thinner than the non-coupling walls of the coupling segment of the adapter. The non-coupling walls are support walls for the coupling walls with thicknesses selected to result in a more uniform contact pressure profile of the coupling surfaces against the sensor housing sensing surfaces. The convex shape of the acoustic coupling surfaces, the varying thickness of the walls of the adapter in the coupling segment and the difference in composition of the adapter and sensing channel result in the more uniform pressure profile of the adapter against the sensing channel of the housing. This configuration provides continuous force of the acoustic coupling surfaces of the adapter against the sensing channel walls of the housing through extended periods of contact pressure and through periods during which heat is experienced.

The adapter is shaped to permit its insertion into the sensor housing in a predetermined orientation. A tab on the adapter fits into a corresponding tab indentation in the sensor housing which not only assures correct orientation, but also guides the adapter into the sensor housing. The tab is mounted on an annular positioning ring which fits into a positioning channel in the housing. The positioning ring and positioning channel prevent longitudinal movement of the adapter such that the mechanical action of the pumping mechanism does not affect the performance of the sensor.

The adapter has an input end, an output end, an acoustic coupling segment between the two and an inner passage interconnecting all three. The inner passage is tapered within the acoustic coupling segment such that it is larger at one end than at the other. Both the input and output ends have means for coupling to fluid line segments.

The housing includes a guide channel above the sensing channel to guide the adapter into the sensing channel during its insertion. The guide channel has walls beveled outward to guide the adapter into the sensing channel during insertion. The beveled walls terminate at the housing sensing surfaces which are acoustically coupled to the transducers. These housing sensing surfaces form part of the sensing channel and contact the adapter acoustic coupling surfaces. The housing sensing surfaces are located at a distance from each other which is less than the distance between the beveled walls at their closest point and create a ledge which the adapter will contact upon insertion. This ledge aids in wiping off any contaminants which may exist on the outer surface of the adapter during its insertion into the sensor housing.

Other aspects and advantages of the invention will become apparent from the following detailed description and the accompanying drawings, illustrating by way of example the features of the invention.

BRIEF DESCRIPTION OF THE DRAWINGS

FIG. 3 is a diagrammatic view of the sensing channel shape;

FIG. 5 is a top view of the adapter of FIGS. 1 and 2; and

FIG. 6 is a cross-section lengthwise view of the adapter of FIGS. 1, 2 and 4.

DETAILED DESCRIPTION OF THE PREFERRED EMBODIMENT

Figures 1, 2:
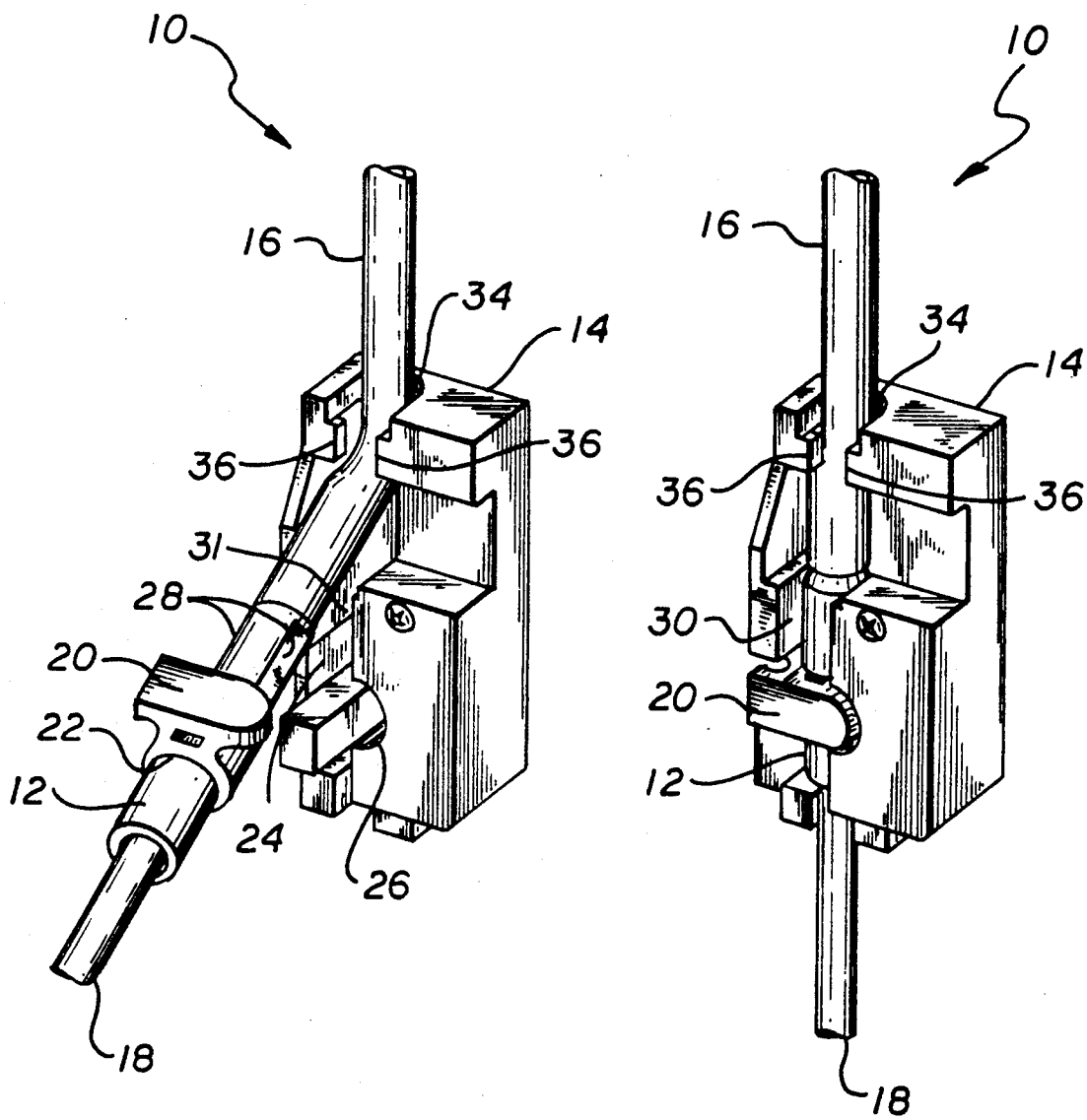
FIG. 1 is a perspective view of an air-in-line sensor in accordance with the principles of the invention showing the upstream line inserted in the housing but the adapter not engaged with the housing.
FIG. 2 is a perspective view of the air-in-line sensor of FIG. 1 showing the adapter and the upstream and downstream lines engaged with the housing.

Referring now to the drawings wherein like reference numerals indicate like or corresponding elements between the different figures, there is shown in FIGS. 1 and 2 a sensor 10 in accordance with the principles of the invention. The sensor 10 comprises an adapter 12 and a sensor housing 14. In both FIGS. 1 and 2, the adapter 12 is coupled to an upstream pumping tube 16 and a downstream tube 18. The upstream tube 16 in one embodiment is formed of silicone and the downstream tube 18 is formed of PVC. The silicone upstream tube 16 may be subjected to the action of a peristaltic pump (not shown) which forces the contents of the fluid line through the upstream tube 16 and the sensor 10 and into the downstream tube 18.

The adapter 12 includes a tab 20 which guides the adapter 12 into a predetermined orientation in the sensor housing 14. The tab 20 is mounted on an oversized annular positioning ring 22 which fits into a positioning channel 24 in the sensor housing 14. The sensor housing 14 includes an indentation 26 to accept the tab 20 of the adapter 12. While the tab 20 assures that the adapter is correctly oriented in the housing vis-a-vis its upstream end, its downstream end and its rotational position, the oversize annular positioning ring 22 and positioning channel 24 function to immobilize the adapter 12 in the sensor housing 14 in the longitudinal direction. This immobility and the composition of the adapter as discussed below operate to isolate the adapter from the mechanical action of the associated upstream peristaltic pump so that deformation of the tubing 16 imposed by the mechanical pumping action will not affect the air-in-line sensor. This also isolates the air-in-line sensor from distal end strain caused by external loading, such as that resulting from patient movement.

The adapter 12 also comprises outwardly facing, slightly convex acoustic coupling surfaces 28 disposed diametrically opposite each other for engaging the sensing channel 30(FIG. 2) of the housing 14 which will be described below in greater detail. In one embodiment, the adapter is formed of "thick" PVC, having a range of thicknesses of 0.050 inches (1.27 mm) to 0.130 inches (3.45 mm) through the adapter as will be discussed further below. This thickness exceeds that of both the upstream 16 and downstream 18 tubes and provides an advantage in the case of the upstream tube 16 in that the mechanical action of the peristaltic pump which deforms the upstream tube 16 will not affect the thicker adapter. The combination of the greater thickness and the immobilization brought about by the positioning ring isolate the adapter 12.

The housing 14 includes two acoustic sensing surfaces or walls 31 disposed opposite each other, which can be seen in greater detail in FIGS. 3 and 4 discussed below, forming part of the sensing channel 24. The sensor housing 14 also includes an upstream tube guide channel 34 comprising a pair of separated tabs 36. The compliant upstream tube 16 is pressed between the tabs 36 and into the tube guide channel 34 as shown in FIGS. 1 and 2 and then the adapter 12 is slid upwards so that part of it resides under the tabs 36.

The tab 20 extends cross-wise across the adapter 12 and has a first and a second end. The sensor housing 14 includes indentations of corresponding shapes to receive both ends of the tab 20. The ends of the tab 20 are shaped differently so that only one orientation of the tab 20 in the sensor housing 14 is possible.

Referring now to FIG. 3, there is shown a side, diagrammatic view of the sensing channel 30 and an adapter guide channel 37 with the adapter inserted. In accordance with another aspect of the invention, the top of each wall of the adapter guide channel 37 includes a beveled section 38 which guides the adapter 12 into the sensing channel 30 during insertion. Each beveled section terminates at housing acoustic sensing walls 31 which are coupled to the transducers 32. The housing sensing walls 31 are separated from each other by a distance which is less than the distance between the beveled walls 38 and ledges 33 result. The distance between the housing sensing walls 31 is less than the diameter of the adapter 12 and an interference fit results. This interference fit will result in the acoustic coupling surfaces of the adapter 12 being "wiped" of exterior contaminants by the ledges during insertion of the adapter 12 into the sensor housing 14. Cleaning this coupling segment results in a more consistent adapter/transducer interface and more accurate air-in-line sensing.

Figure 4:
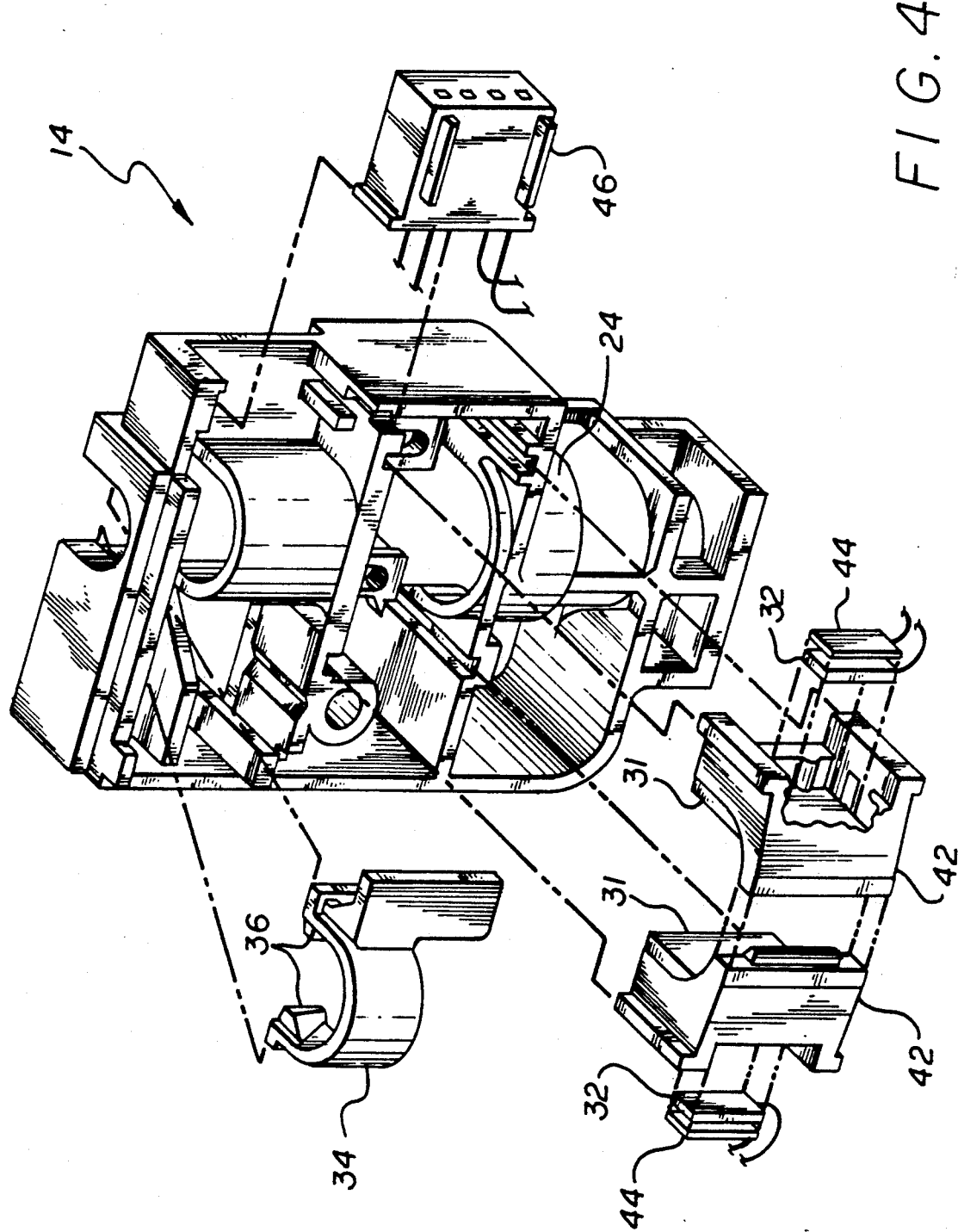
FIG. 4 is an exploded view of the sensor housing assembly of FIGS. 1 and 2 shown from behind.

Referring now to FIG. 4, an exploded back view of the sensor housing 14 assembly is shown. The housing 14 comprises two transducers 32 which may be standard piezoelectric crystals used for radiating, receiving and conducting acoustic energy. These transducers 32 may be glued onto the backs of the housing sensing coupling walls 31 with epoxy as shown by the dashed lines. The sensing walls 31 form part of two sensing nests 42 which mate together. Backing each transducer 32 is a Corprene® cork barrier 44 used for acoustic isolation of the transducers 32. The area behind each barrier 44 may be back-filled with silicone rubber. The sensing nests 42 are then bonded into position in the housing 14 as shown by the dashed lines to form the sensing channel 30. Also shown is a connector 46 used for connecting the wires of the transducers 32 to outside signal lines.

Referring now to FIG. 5, a top view of the adapter 12 is shown. The tab 20 is formed integrally with the oversize annular positioning ring 22. The adapter 12 comprises acoustic coupling surfaces 28 each of which has a slightly convex shape and which are located diametrically opposite each other. These sides 28 are used to engage the housing sensing walls 31 and thereby couple to the transducers 32.

The concentric circles depicted inside the coupling surfaces 28 in FIG. 5 are described in reference to FIG. 6 as follows. The inner-most circle represents the smaller end of the tapered inner wall 52. The next outer circle represents the larger end 54 of the tapered inner wall. The next circle represents the beginning of the lead-in radius 56 formed on the proximal end of the adapter 12. The next circle represents the outer surface 59 of the adapter adjacent the tab 20. Although the outer surface of the adapter from its proximal end, indicated generally by the numeral 60, is tapered somewhat, it is indicated only by numeral 59. As shown in FIG. 6, the acoustic coupling segment is indicated generally by numeral 58.

Referring to FIGS. 3 and 5, as discussed above, the adapter coupling surfaces 28 and the sensing channel 30 are shaped so that an interference fit results between the two in which a more uniform pressure profile is established. Such a pressure profile provides better acoustic coupling under the variety of conditions which may be experienced by the air-in-line sensor. In the embodiment disclosed, the sensor channel comprises straight sensing walls 31 formed of a rigid material. The coupling walls 28 of the adapter are slightly convex in shape and the adapter is formed of a semicompliant material.

The walls of the coupling surfaces 28 are thinner than the non-coupling walls 57 in the coupling segment of the adapter. These thicker, non-coupling walls 57 provide support to the walls of the coupling surfaces 28 to obtain a better contact pressure profile between the coupling surfaces 28 and the sensing walls 31 of the housing 14. In that regard, they are support walls and their thickness is selected to provide support to the coupling surfaces throughout the temperature range and the extended periods of contact pressure to be experienced by the air-in-line sensor 10. In one embodiment, the radius of the coupling surfaces 28 was 0.35 in. (8.89 mm) and the radius of the outer surfaces of the support walls was 0.142 in. (3.6 mm). The center for the radius of the support walls was co-located with the center of the inner passage of the adapter while the centers for the radii of the coupling surfaces were located on the dashed line in FIG. 5 (indicating the section of FIG. 6) at positions removed from the center of the inner passage of the adapter.

The inside surface of the adapter 12 is circular, although tapered along the longitudinal axis, while the outside surface is non-circular. The walls of the adapter are thicker at the support walls 57. As mentioned, this configuration has been found to provide the more uniform contact pressure profile discussed above. Upon insertion of the adapter 12 into the sensing channel 30, contact with the sensing walls 31 deforms the thinner walls of the adapter comprising the convex coupling surfaces 28 inward although the coupling surfaces 28 continue to apply pressure outward against the sensing channel walls 31. Due in part to the support provided by the support walls 57, the coupling surfaces 28 maintain a more uniform pressure profile against the housing sensing walls 31 during deformation and are not over-compressed.

In this embodiment, the adapter is formed of a semi-compliant material, and the channel is rigid. However, in another embodiment, the adapter may be rigid and the channel semi-compliant.

Referring now to FIG. 6, a cross-section lengthwise view of the adapter 12 is shown. The internal passage of the adapter 12 is tapered from the upstream end 54 to the tab 20 position 52 with the upstream end having the larger diameter of the taper. The taper extends through the acoustic coupling segment 58 of the adapter 12 which includes the convex coupling surfaces 28 for contact with the sensing walls 31 of the sensing channel 30. This tapered passage 54 to 52 through the acoustic coupling segment 58 of the adapter 12 results in a variable velocity of the fluid moving through the adapter 12. It has been found that this taper improves the movement of air bubbles through the coupling segment 58. The higher velocity of the fluid downstream resists an air bubble from attaching itself to the inside wall and growing larger. It also resists the tendency of an air bubble to detach itself from the wall downstream and float upstream past the coupling segment 58. It is believed that the variable velocity overcomes the surface tension along the wall of tube. In one embodiment, the taper was ½° draft per side.

In the embodiment shown in FIG. 6, the outside surface of the adapter 12 has a radius 56 formed on the upstream end 60 so that the upstream tube 16 may be slid over the adapter 12 and held in place by a press fit. The upstream segment of the adapter 12 is also tapered from the upstream end 60 to the beginning of the coupling segment 58 somewhat. The downstream end 62 of the adapter 12 has a tapered opening so that the downstream tube 18 may be slid into the adapter into position. A stop 50 is formed in the inside passage to stop insertion of the downstream tube 18 beyond the point of the stop. This particular connection configuration of the adapter to the upstream and downstream tubes is by way of example only, other configurations are possible as will be recognized by those skilled in the art.

From the foregoing, it will be appreciated that the air-in-line sensor in accordance with the principles of the invention provides for positive and firm sensor engagement. The tubing adapter, which forms part of the tubing line, is resistant to fluid contamination residing on the outside surfaces of the adapter and the adapter is resistant to air bubbles within the tubing from becoming transfixed or from oscillating in the fluid stream past the transducers.

Although specific embodiments of the invention have been described and illustrated it is clear that the invention is susceptible to numerous modifications and embodiments within the ability of those skilled in the art, and without the exercise of the inventive faculty. Thus, it should be understood that various changes in form, detail and application of the present invention may be made without departing from the spirit and scope of the invention.

We claim:

1. A sensor for sensing a fluid line, the sensor comprising:
    a fluid line adapter inserted in the fluid line, the adapter having first and second ends and adapted to attach at both ends to the fluid line and having an inner passage which is in fluid communication with the fluid line, the adapter having a coupling segment comprising two coupling surfaces located diametrically opposite each other, the adapter further comprising an orientation tab; and
    a sensor housing, the housing comprising:
        an indentation which receives the orientation tab of the adapter in a predetermined orientation;
        a sensor channel comprising sensing walls which recieve the coupling surfaces of the adapter, the distance between the sensing walls being less than the diameter of the coupling surfaces of the adapter; and
        first and second transducers spaced apart across the channel which communicate sensing energy through the adapter.

2. The sensor of claim 1 wherein:
    the coupling surfaces are formed on coupling walls of the coupling segment of the adapter and the walls adjoining the coupling walls are support walls;
    wherein the support walls are thicker than the coupling walls.

3. The sensor of claim 2 wherein the support walls have a thickness selected to provide a predetermined pressure profile of the coupling surfaces against the sensing walls of the sensor channel.

4. The sensor of claim 1 wherein the adapter is formed of a semi-compliant material while the sensing walls of the sensor channel are rigid.

5. The sensor of claim 1 wherein:
    the coupling surfaces of the adapter are convex; and
    the sensing walls are parallel and straight.

6. The sensor of claim 1 further comprising a pair of ledges disposed above the sensing walls, the ledges are spaced apart by a distance which is less than the diameter of the coupling surfaces of the adapter, the ledges are adapted to receive the sensing surfaces of the adapter and thereby wipe off contaminants on the adapter during insertion of the adapter into the housing.

7. The sensor of claim 1 wherein the inner passage of the coupling segment of the adapter is tapered.

8. The sensor of claim 7 wherein the proximal opening of the inner passage through the coupling segment is larger than the distal opening of the coupling segment.

9. The sensor of claim 1 wherein the fluid line adapter is inserted in the fluid line in a series arrangement so that an upstream fluid line is connected to the proximal end of the adapter and a downstream fluid line is connected to the distal end of the adapter.

10. The sensor of claim 1 wherein the adapter is formed of a semi-compliant material and the coupling surfaces are convex;
    the sensing walls of the housing are formed of a rigid material and are straight;
    whereby the coupling surfaces of the adapter are reshaped to conform to the sensing walls.

11. A sensor for sensing a fluid line, the sensor comprising:
    a fluid line adapter inserted in the fluid line in a series arrangement so that an upstream fluid line is connected to the proximal end of the adapter and a downstream fluid line is connected to the distal end of the adapter, the adapter having an inner passage which is in fluid communication with the fluid line, the adapter having a coupling segment comprising two coupling surfaces located diametrically opposite each other, the coupling surfaces are formed on coupling walls of the coupling segment of the adapter and the walls adjoining the coupling walls are support walls, the adapter further comprising an orientation tab; and
    a sensor housing, the housing comprising:
        an indentation which receives the orientation tab of the adapter in a predetermined orientation;

a sensor channel comprising sensing walls which receive the coupling surfaces of the adapter, the distance between the sensing walls being less than the diameter of the coupling surfaces of the adapter; and first and second transducers spaced apart across the channel which communicate sensing energy through the adapter;

wherein the support walls have a thickness selected to provide a predetermined pressure profile of the coupling surfaces against the sensing walls of the sensor channel.

12. The sensor of claim 11 wherein the inner passage of the coupling segment of the adapter is tapered.

13. The sensor of claim 12 wherein the proximal opening of the inner passage through the coupling segment is larger than the distal opening of the coupling segment.

14. The sensor of claim 12 wherein the adapter is formed of a semi-compliant material and the coupling surfaces are convex;

the sensing walls of the housing are formed of a rigid material and are straight;

whereby the coupling surfaces of the adapter are reshaped to conform to the sensing walls.

15. The sensor of claim 12 further comprising a pair of ledges disposed above the sensing walls, the ledges are spaced apart by a distance which is less than the diameter of the coupling surfaces of the adapter, the ledges are adapted to receive the sensing surfaces of the adapter and thereby wipe off contaminants on the adapter during insertion of the adapter into the housing.

16. A sensor for sensing a fluid line, the sensor comprising:

a fluid line adapter inserted in the fluid line in a series arrangement so that an upstream fluid line is connected to the proximal end of the adapter and a downstream fluid line is connected to the distal end of the adapter, the adapter having an inner passage which is tapered and which is in fluid communication with the fluid line, the adapter having a coupling segment comprising two coupling surfaces located diametrically opposite each other, the coupling surfaces are formed on coupling walls of the coupling segment of the adapter and the walls adjoining the coupling walls are support walls, the adapter further comprising an orientation tab and a positioning ring; and a sensor housing, the housing comprising:

an indentation which receives the orientation tab of the adapter in a predetermined orientation;

a positioning channel which receives the positioning ring of the adapter to resist longitudinal movement of the adapter in the sensor housing;

a sensor channel comprising sensing walls which receive the coupling surfaces of the adapter, the distance between the sensing walls being less than the diameter of the coupling surfaces of the adapter; and first and second transducers spaced apart across the channel which communicate sensing energy through the adapter;

wherein the support walls have a thickness selected to provide a predetermined pressure profile of the coupling surfaces against the sensing walls of the sensor channel.

17. The sensor of claim 16 wherein the adapter is formed of a semi-compliant material while the sensing walls of the sensor channel are rigid.

18. The sensor of claim 17 wherein:

the coupling surfaces of the adapter are convex; and the sensing walls are parallel and straight.

19. The sensor of claim 16 further comprising a pair of ledges disposed above the sensing walls, the ledges are spaced apart by a distance which is less than the diameter of the coupling surfaces of the adapter, the ledges are adapted to receive the sensing surfaces of the adapter and thereby wipe off contaminants on the adapter during insertion of the adapter into the housing.

* * * * *